United States Patent [19]

Edgren et al.

[11] Patent Number: 5,718,700
[45] Date of Patent: Feb. 17, 1998

[54] EXIT MEANS IN DOSAGE FORM

[75] Inventors: David Emil Edgren, El Granada; Robert Raymond Skluzacek, Newark; Brian L. Barclay, Sunnyvale; Gurdish Kaur Bhatti, Fremont, all of Calif.

[73] Assignee: ALZA Corporation, Palo Alto, Calif.

[21] Appl. No.: 309,389

[22] Filed: Sep. 20, 1994

[51] Int. Cl.$^6$ .................................................... A61K 9/22
[52] U.S. Cl. ........................ 604/892.1; 424/453; 424/472; 424/473
[58] Field of Search ................... 604/891.1, 892.1; 424/422–424, 456–461, 472, 473

[56] References Cited

U.S. PATENT DOCUMENTS

| | | |
|---|---|---|
| 3,845,770 | 11/1974 | Theeuwes et al. . |
| 3,916,899 | 11/1975 | Theeuwes et al. . |
| 4,063,064 | 12/1977 | Sauders et al. . |
| 4,088,864 | 5/1978 | Theeuwes et al. . |
| 4,200,098 | 4/1980 | Ayer et al. ................ 424/473 X |
| 4,210,139 | 7/1980 | Higuchi .................... 424/473 X |
| 4,271,113 | 6/1981 | Luschen et al. . |
| 4,449,983 | 5/1984 | Cortese et al. ............... 604/892.1 |
| 4,743,248 | 5/1988 | Bartoo et al. ............... 604/892.1 |
| 4,842,867 | 6/1989 | Ayer et al. .................. 424/473 |
| 4,857,330 | 8/1989 | Stephens et al. ............ 424/424 |
| 5,071,607 | 12/1991 | Ayer et al. . |
| 5,108,756 | 4/1992 | Curatolo .................... 424/450 |
| 5,226,902 | 7/1993 | Bae et al. ................... 607/892.1 |
| 5,240,713 | 8/1993 | Ayer ......................... 424/473 |
| 5,324,280 | 6/1994 | Wong et al. ................ 604/892.1 |
| 5,358,721 | 10/1994 | Guittard et al. ............. 424/473 |
| 5,498,255 | 3/1996 | Wong ........................ 604/892.1 |

Primary Examiner—Michael Powell Buiz
Assistant Examiner—A. T. Nguyen
Attorney, Agent, or Firm—Paul L. Sabatine; Michael J. Rafa; John A. Dhuey

[57] ABSTRACT

A dosage form is disclosed comprising a wall that surrounds a bilayer core with exit passageway for communicating with the bilayer core in the wall.

9 Claims, 1 Drawing Sheet

EXIT MEANS IN DOSAGE FORM

FIELD OF THE INVENTION

This invention pertains to a dosage form. More particularly, the invention concerns a dosage form comprising a wall possessing at least one side that surrounds a compartment containing a drug layer and a push layer, which dosage form is characterized by exit means on the side that communicates with the drug layer and the push layer.

BACKGROUND OF THE INVENTION

Dosage forms comprising exit means for releasing a drug from the dosage are known to the pharmaceutical and medical arts. Dosage forms comprising drug-releasing exit means are known in U.S. Pat. Nos. 3,845,770 issued to Theeuwes et al; 3,916,899 issued to Theeuwes et al; 4,063,064 issued to Saunders et al; 4,088,864 issued to Theeuwes et al; 4,218,433 issued to Kooichi et al; 4,271,113 issued to Luschen; 5,071,607 issued to Ayer et al; and 5,256,440 issued to Appel et al Dosage forms comprising a wall that surrounds a compartment containing a drug layer in contact with a push layer and having an exit orifice in communication with just the drug layer are known in U.S. Pat. Nos. 4,327,725 issued to Cortese et al; 4,612,008 issued to Wong et al; 4,765,989 issued to Wong et al; 4,783,337 issued to Wong et al; 4,814,181 issued to Jordan et al; 4,837,111 issued to Deters et al; 4,915,953 issued to Jordan et al; and, 4,915,954 issued to Ayer et al.

The present prior art dosage forms comprising two layers consisting of both a drug layer and a push layer are provided with a single exit orifice in contact with the drug layer for releasing a drug from the dosage form. The current method for manufacturing in the wall of the dosage form an exit orifice consists in detecting a color difference between the drug layer and the push layer followed by forming the exit orifice on the prescribed drug layer surface, that is, the drug layer side. It is self-apparent a need exists to provide a dosage form and a method for manufacturing an exit orifice in the dosage form that eliminates the need to discriminate between the surface of the drug layer and the push layer, during the manufacture of the dosage form. The need exists to eliminate the need to formulate a different colored drug layer from a push layer. The need exists also to allow the exit orifice to be formed in a final production operation, after the wall or an overcoat is formed on the dosage form.

OBJECTS OF THE INVENTION

Accordingly, in view of the above presentation, it is an immediate object of this invention to provide a dosage form comprising an exit orifice that substantially overcomes the deficiencies and the omissions associated with the prior art.

Another object of the invention is to provide a dosage form that eliminates the need to provide colored layers and eliminates the need to differentiate between colored and noncolored layers.

Another object of the invention is to provide a dosage form comprising an exit port formed in the final production operation after the application of a wall, or after the application of a wall and an overcoat around an inner bilayer core of a dosage form.

Another object of the invention is to provide a dosage form comprising a wall that surrounds a bilayer core consisting of a first drug layer and a second push layer with an exit means in the wall that connects the drug layer and the push layer with the exterior of the dosage form.

Another object of the invention is to provide a dosage form comprising a wall that surrounds an inner drug layer an inner push layer with an exit in the wall that connects the drug layer and the push layer with the outside of the dosage form, which dosage form is characterized in operation of releasing the drug layer with the push layer remaining in the dosage form.

Another object of the present invention is to provide an improvement in a dosage form, wherein the dosage form comprises a semipermeable wall that surrounds a drug formulation layer and a push layer, and wherein the improvement comprises exit means in the semipermeable wall communicating with the drug formulation layer and the push layer with the dosage form selectively releasing the drug formulation through the exit means to a biological receptor for the drug therapy.

Another object of the invention is to provide a method for producing drug therapy in an animal by administering a drug to the animal from a dosage form comprising a compartment containing a drug formulation and an expandable driving member, which drug formulation is administered through an exit means that communicates with the drug layer in the compartment while concomitantly maintaining the expandable driving member in the dosage form.

Other objects, features, and advantages of the invention will be apparent to those skilled in the dispensing arts from the following detailed specification, taken in conjunction with the drawing figures and the accompanying claims.

BRIEF DESCRIPTION OF THE DRAWINGS

In the drawing figures, which are not drawn to scale, but are set forth to illustrate various novel embodiments of the invention, the drawing figures are as follows.

Drawing

Drawing

Drawing

In the drawing and in the specification, like parts in related drawing figures are identified by like numbers. The terms appearing earlier in the specification and in the description of the drawings, as well as in embodiments thereof, are further described elsewhere in the disclosure.

DETAILED DESCRIPTION OF THE DRAWING FIGURES

Figure 1:
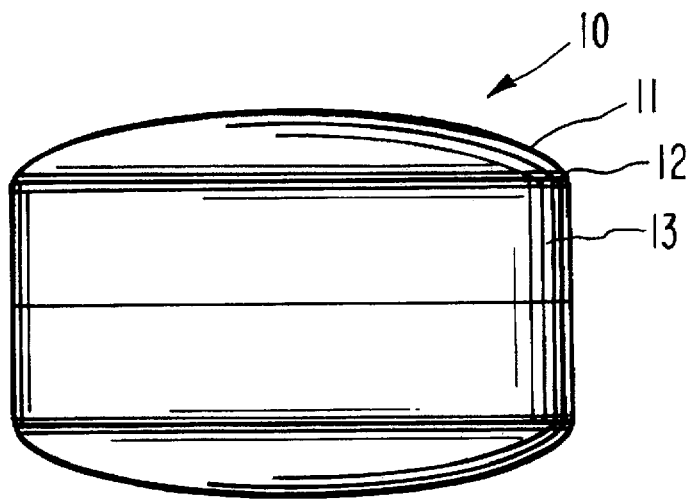
FIG. 1 is a view of a dosage form provided by the invention, which dosage form is adapted, shaped and sized for orally administering a drug to the gastrointestinal tract of an animal including a human.

Turning now to the drawing figures in detail, which drawing figures are representative examples of dosage forms provided by the invention, and which examples are not to be constructed as limiting, one example of the dosage form is illustrated in drawing FIG. 1, by the numeral 10. In drawing FIG. 1, dosage form 10 comprises a body member 11, that comprises a wall 12, that surrounds and encloses an internal compartment, not seen, in drawing FIG. 1. Dosage form 10 comprises a side or surface 13 that projects around dosage form 10, defined by the depicted structural lines.

Figure 2:
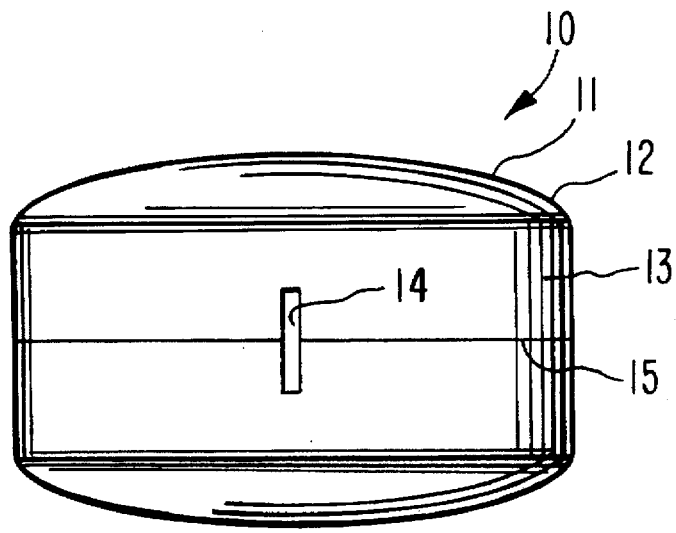
FIG. 2, illustrate the dosage form of drawing FIG. 1 and depicts further an exit member on a side of the dosage form.

In drawing FIG. 2, dosage form 10 is seen comprising body 11, wall 12, side 13, and exit means 14. The exit means 14 connects an internal compartment, not seen, with the exterior of dosage form 10. Exit means 14 connects an internal bilayer core, not seen, but represented by line 15 with the biological environment of uses. Exit means 14 is sized and shaped for releasing a drug formulation from bilayer core, while simultaneously restricting, or essentially minimizing the passage of a push composition layer from dosage form 10. Exit means 14 possesses a shape and opening that communicates with a drug composition layer and a push composition layer inside dosage form 10. The exit means 14 can have any shape that embraces both the drug composition layer and the push composition layer. The exit means 14 includes an elongated aperture, a stretched passageway, a lengthened incision, a hole long in proportion to width, a long narrow cut, a long slender opening, a passageway extended in length, and a slit possessing a length greater than it width. The exit member can be formed by mechanical cutting of the wall, by laser cutting, by eroding a preshaped erodible polymer such as polyglycolic acid, polylactic acid, erodible polyorthoester, or erodible polyorthocarbonate in the wall, or by leaching a selected area saturated with leachable materials like sorbitol, fructose, maltose or lactose from the wall. Techniques for forming an exit means are disclosed in U.S. Pat. Nos. 3,845,770; 3,916,899; 4,063,064; 4,088,864; 4,200,098; and 4,285,987.

Figure 3:
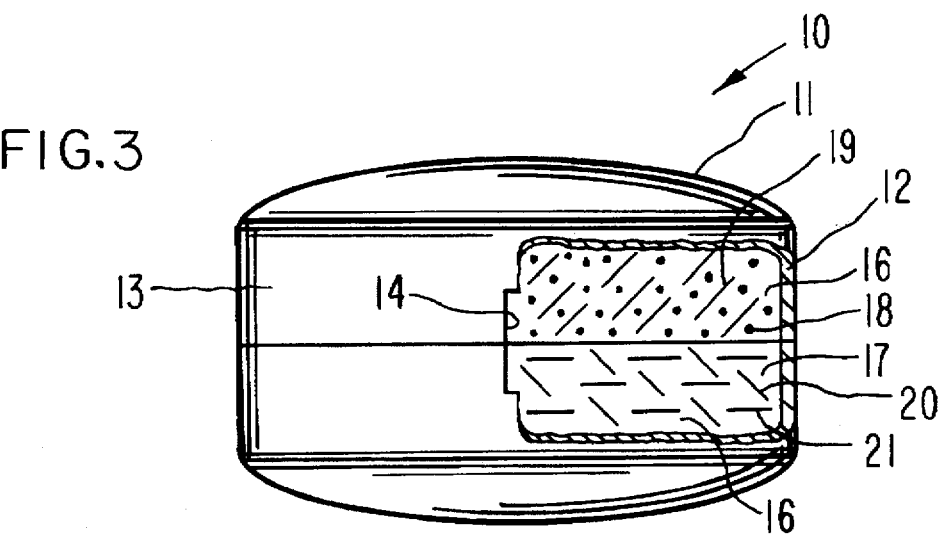
FIG. 3 is an opened view of the dosage form of drawing FIG. 2 illustrating the general and the internal structure of the dosage form.

In drawing FIG. 3, dosage form 10 is seen in opened view, comprising body 11, wall 12, side 13 and exit means 14. Wall 12 of dosage form 10, comprises a semipermeable composition that is permeable to the passage of an exterior aqueous fluid, or a biological aqueous fluid present in an environment of use, and wall 12 is substantially impermeable to the passage of a drug and other ingredients present in dosage form 10. The expression environment of use includes animals and humans. Wall 12 surrounds and defines an internal compartment 16. The composition comprising wall 12 is substantially inert, nontoxic, and wall 12 maintains its physical and chemical integrity during the drug dispensing life of dosage form 10. The phrase keeps its physical and chemical integrity means wall 12 does not lose its structures, and wall 12 does not change chemically during the dispensing life of dosage form 10.

Wall 12 comprises a cellulosic polymer composition. The cellulosic polymer comprises a member selected from the group consisting of a cellulose ester-ether, cellulose acylate, cellulose diacylate, cellulose triacylate, cellulose acetate, cellulose diacetate, and cellulose triacetate. The cellulosic polymers can comprise a degree of substitution, D.S., on the anhydroglucose unit from greater than 0 up to 3, inclusive. By degree of substitution is meant the average number of hydroxyl groups originally present on the anhydroglucose unit comprising the cellulose polymer that are replaced by a substituting group. Exemplary polymers comprise cellulose acetate having a D.S. up to 1 and acetyl content up to 21 weight cellulose acetate having an acetyl content of 32 to 39.8%; cellulose diacetate having a D.S. of 1 to 2 and an acetyl content of 21 to 35%; cellulose triacetate having a D.S. of 2 to 3 and an acetyl content of 35 to 44.8%, and the like. Other examples comprise cellulose propionate having a D.S. of 1.8, a propanol content of 39.2% to 45% and a hydroxyl content of 2.8% to 5.4%; cellulose acetate butyrate having a D.S. of 1.8, an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose triacylates having a D.S. of 2.9 to 3 such as cellulose trivalerate, cellulose trilaurate, cellulose tripalmitate, cellulose trisuccinate, and cellulose triooctanoate; cellulose diacylates having a D.S. of 2.2 to 2.6 such as cellulose disuccinate, cellulose dipalmitate, cellulose dioctanoate, cellulose dipentale, and the like. Additional cellulosic polymers comprise ethyl cellulose comprising an ethoxy group degree of substitution of 1.5 to 3, about 40% to 50% ethoxy content, and the like. In one preferred manufacture wall 12 comprises 100 weight percent (wt. %) of a cellulosic polymer disclosed above. In another manufacture wall 12 can comprise from 60 weight percent to 100 weight percent of a cellulose polymer as disclosed above, from 0 weight percent to 30 weight percent of a member selected from, the group consisting of a acellulose ether selected from the group consisting of hydroxyalkylcellulose, hydroxypropylcellulose, hydroxypropylmethylcellulose and hydroxyethylcellulose; and from 0 weight percent to 30 weight percent of polyethylene glycol; with the total amount of all components comprising wall 12 equal to 100 weight percent. The cellulosic polymers are known in U.S. Pat. Nos. 3,133,132; 3,845,770; 3,916,899 and 4,160,000; and in the *Handbook of Common Polymers* by Scott, J. R. and Roff W. J., (1971) published by CRC Press Cleveland, Ohio.

Internal compartment 16 comprises a first or drug layer 18 and a second or push layer 17. The first drug layer 18, and the second or push layer 17 initially are in bilaminar arrangement, and then cooperate with each other and with dosage form 10 for delivering a dose of 10 ng to 1200 mg of drug 18, in an effective dose per unit time from dosage form 10. Drug 18 is present in compartment 16 with a drug dispensing polymer composition 19. The dispensing polymer comprises a poly(alkylene oxide) wherein the alkylene consists of 1 to 7 carbons and a molecular weight of 25,000 to 375,000 grams per mole represented by 25 mg to 800 mg of poly(methylene oxide), poly(ethylene oxide), poly (propylene oxide), poly(hexylene oxide) and poly(heptylene oxide); a hydroxypropylalkylcellulose having a molecular weight of 9,000 to 75,000 as represented by 10 ng to 70 mg of hydroxypropylmethylcellulose, hydroxypropylethylcellulose, hydroxypropylisopropylcellulose; and 0 mg to 20 mg of a poly(vinylpyrrolidone) possessing a 7,500 to 75,000 molecular weight; and a 0 mg to 150 mg of a carboxyvinylpolymer of 10,000 to 400,000 molecular weight. The first or drug layer 18 can comprise 0 mg to 10 mg of a lubricant such as magnesium stearate or stearic acid; and 0 mg to 5.0 mg of a surfactant selected from the group consisting of nonionic, anionic, and ionic surfactants.

The second or push layer 17 comprises a composition that imbibes, absorbs an aqueous fluid, expands and pushes drug layer 18 from dosage form 10. The second layer 17 comprises 0 mg to 400 mg of a high moelcular weight osmopolymer either crosslinked with ionic or covalent bonds or not crosslinked of 2,000,000 to 8,000,000 molecular weight such as poly(alkylene) oxide of 2,500,000 to 7,775,000 molecular weight as represented by poly(alkylene oxide) selected from the group consisting of poly(methylene oxide), poly(ethylene oxide), poly(propylene oxide), poly (butylene oxide), poly(pentylene oxide) poly(hexylene oxide) and poly(heptylene oxide) with the poly(alkylene oxide) of the push layer possessing a higher molecular, weight than the drug layer 18, 0 to 400 mg of a carboxyalkylcellulose salt such as sodium carboxymethylcellulose, potassium carboxymethylcellulose or lithrum carboxymethylcelluylose having a 60,000 to 700,000 molecular weight; 0 mg to 200 mg of a carboxyvinyl polymer of 550,000 to 5,000,000 molecular weight with the carboxyvinyl polymer possessing a higher molecular weight than the corresponding carboxyvinyl polymer in drug layer 18 both polymers represented by dash 21;0 to 150 mg of an osmagent 20 selected from sodium chloride, potassium chloride and the like; 0 to 40 mg of a tabletting binder such as hydroxypropyl methylcellulose having a molecular weight of 9,600 to 15,000; 0 mg to 5 mg of a tabletting lubricant such as magnesium stearate; and 0 mg to 5 mg of a ferric oxide.

In the specification and the accompanying claims, the term drug includes any physiologically or pharmacologically active substance that produces a local or systemic effect when administered to the gastrointestinal tract of a human. Representative of drugs include drugs acting at synaptic and neuroeffector junctional sites including neurolhumoral transmission, the autonomic and somatic motor nervous systems, cholinergic agonists, anticholinesterases, drugs acting at the neuromuscular junction and autonomic ganglia, catecholamine and sympathomimetic drugs, and adrenergic receptor antagonists; drugs acting on the central nervous system, neurohumoral transmission, anesthetics, hypnotic and sedatives, drugs for psychiatric disorders, drugs for the therapy of epilepsies, drugs for Parkinson's disease, analgesics and antagonists; autocoids, drugs for inflammation; drugs affecting renal function and electrolyte metabolism; cardiovascular drugs, renin, angiotensin, calcium-channel blockers, adrenergic antagonists, antihypertensive drugs, cardiac glycosides, antiarrhythmic drugs and drugs used in hyperliproteninimas; drugs affecting gastrointestinal function, drugs for gastric acidity, and for treating peptic ulcers; drugs affecting uterine motility; drugs as chemotherapy of parasitic infections; drug therapy of microbial diseases; drug therapy of neoplastic diseases; drugs for immunosuppression; hormones; hormones; hormones antagonists; and vitamins.

The drugs can be in various forms such as uncharged molecules, molecular complexes, pharmacologically acceptable salts such as hydrochloride, hydrobromide, sulfate, laurylate, palmitate, phosphate, nitrate, borate, acetate, maleate, tartrate, oleate, and salicylate. For acid drugs, salts of metals, amines, or organic cations, for example quaternary ammonium can be used. Derivatives of drugs such as esters, ethers, and amides can be used. A drug that is water insoluble can be in a form that is a water soluble derivative thereof to serve as a solute, and on its release from the dosage form is converted by enzymes, hydrolyzed by the body pH, or by other metabolic processes to a biologically active form. The beneficial drugs are known to the pharmaceutical and medical arts in *Pharmaceutical Sciences*, by Remington, 14th Ed., 1979, published by Mack Publishing Co., Easton, Pa.; *The Drug, The Nurse, The Patient, Including Current Drug Handbook*, by Falconer, et al, published by Saunder Company, Philadelphia, Pa.; *Medicinal Chemistry*, 3rd Ed., Vol. 1 and 2, by Burger, published by Wiley-Inter-Science, NY; and, *The Pharmacological Basis of Therapeutics*, by Goodman and Gilman, 8th Ed., Pergamon Press, NY.

Dosage form 10 of this invention is manufactured by standard techniques. For example, in one manufacture a drug is mixed with a composition forming ingredients and then pressed into a solid, first drug layer possessing dimensions that correspond to the internal dimensions of the compartment. In another manufacture, a drug and other composition forming ingredients and a solvent are mixed into a solid, or into a semisolid, by conventional methods such as ballmilling, calendering, stirring, or rollmilling, and then pressed into a preselected layer-forming shape. Next, a push composition comprising the expandable osmopolymer and other push layer forming ingredients such as an osmagent are homogeneously blended, then pressed into a layer possessing the dimensions of the drug layer and placed into contacting arrangement with the drug layer to provide a bilayer core. In another manufacture the push layer comprising an expandable osmopolymer and other ingredients am mixed and placed in contact with the drug layer, and the two layers pressed into a bilaminated core, and then surrounded with a semipermeable wall. The bilamination of the drug layer and the push layer can be accomplished by using a two-layer press. The semipermeable wall can be applied by molding, spraying or dipping the pressed shaped bilayer core into a wall forming formulation. Another technique that can be used for applying the wall is an air suspension coating procedure. The procedure consists in suspending and tumbling the two layered laminate in a current of air until the wall forming composition surrounds the bilaminated core. The air suspension procedure is described in U.S. Pat. No. 2,799,241; in *J. Pharm. Assoc.*, Sci. Ed., Vol. 48 pp 451–59 (1959); and ibid., Vol. 49, pp 82–84, (1960). Other standard manufacturing procedures are described in *Modern Plastics Encyclopedia*, Vol. 46, pp 62–70, (1969); and in *Pharmaceutical Sciences*, by Remington, 14th Ed., pp 1626–1978, (1970).

The exit means is manufactured by the techniques supra, This invention unexpectedly allows the exit means to be easily positioned on the dosage form. The exit means can be positioned along the peripheral edge or side of the dosage form. In the prior art, in contrast, a single round hole must be centered on the face of the dosage form, and if it is not centered the offset hole may be cosmetically unacceptable, and the offset can lead to an unknown delivery of a drug. A side exit means, for example, is less noticeable, and it produces a cleaner, less-cluttered printing surface for an identifying logo. The invention exit means can enhance a higher cumulative delivery of drug while maintaining a zero-order sustained release rate over a prolonged time of thirty hours. The invention in the exit means imparts safety to the dosage form becomes a collapsible dosage form that can flatten by peristaltic gastrointestinal mobility, and thereby reducing the likelihood of internal intestinal blockage of the spent dosage form.

Exemplary solvents suitable for manufacturing the wall, the laminate, and laminae, comprise inert inorganic and organic solvents that do not adversely affect the final wall and the final laminates. The solvents broadly comprise a member selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents comprise water, acetone, diacetone, alcohol, methanol, ethanol, isopropyl alcohol, butyl alcohol, methyl acetate, ethyl acetate, isopropyl acetate, n-butyl acetate, methyl isobutyl ketone, methylpropyl ketone, n-hexane, n-heptane, ethylene glycol monoethyl ether, ethylene glycol monoethyl acetate, methylene dichloride, ethylene dichloride, propylene dichloride, acetone and water, acetone and methanol, acetone and ethyl alcohol, methylene dichloride and methanol, ethylene dichloride and methanol, and the like.

DETAILED DISCLOSURE OF EXAMPLES OF THE INVENTION

The following examples are merely illustrative of the present invention, and they should not be considered as limiting the scope of this invention in any way, as these examples and other equivalents thereof will become apparent to those versed in the art in the light of the present disclosure, the drawings and the accompanying claims.

EXAMPLE 1

A dosage form adapted, designed and shaped as a drug delivery device for delivering a drug to the gastrointestinal tract of a human is prepared as follows: first, a drug granulation is prepared comprising 400 g of nifedipine, 1490 g of poly(ethylene oxide) of 200,000 molecular weight, and 100 g of hydroxypropylmethylcellulose of 9,200 molecular weight by sieving each ingredient separately through a 40 mesh screen, and then blending together all the ingredients for 5 minutes in a V-blender. Next, anhydrous ethanol is added to the V-blender until approximately 1 liter of ethanol is added to the blend. The wetted mass is allowed to mix for an additional 5 minutes. The wet granulation is removed from the blender and milled to 16-mesh in a fluid air mill. The resultant milled material is spread on white covered oven trays and placed in a forced-air oven at 40° C. The drying is continued overnight. The dried material is milled agan to 16-mesh in a fluid air mill. The granulation is placed back in the V-blender where 10 g of magnesium stearate is added thereto. Next, blending is continued for 3 minutes, to provide a drug composition.

Next, a push composition is prepared as follows: first, 1,286 g of poly(ethylene oxide) of 5,000,000 molecular weight, 584 g of sodium chloride, 100 g of hydroxypropylmethylcellulose of 11,200 molecular weight, and are sieved through a 40-mesh screen, and then blended together in a V-blender. Then, anhydrous ethanol is added through the V-blender until approximately 1.3 liters of the alcohol is added to the blender. The just prepared wetted mass is mixed for an additional 5 minutes. The set mass is milled, dried and remilled as described in the above drug composition preparation. Next, 10 g of magnesium stearate is added to the granulation and blended for 3 minutes in the blender. The completed composition is used to provide the push layer of a bilayer core.

Next, a bilayer core is prepared using a bilayer press, wherein a 11/32 inch (0.135 cm) diameter standard concave tool is used to provide the bilayer core. First, 165 mg of the drug composition is packed into the die, followed by 82.5 mg of the push composition, which are pressed together in bilayer arrangement under 2.5 ton-force.

The bilayered arrangements are coated with a semipermeable wall. The wall forming composition comprises 95% cellulose acetate having an acetyl content of 39.8% and 5% polyethylene glycol having a molecular weight of 3350. The wall-forming composition is dissolved in an acetone-water (95:5 wt:wt) cosolvent to make a 4% solids solution. The wall-forming composition is sprayed onto and around the bilayers in a 24 inch (60 cm) pan coater. Next, an exit slit is laser cut through the semipermeable wall connecting the drug layer and the push layer with the outside of the dosage form. The slit exit is 0.30 mm in width and 20 mm in length. The slit exit port has a mean release rate of 1.8 mg/hr of drug over a 18 hr drug delivery period.

EXAMPLE 2

The procedure disclosed above is followed to provide a dosage form comprising a drug layer weighing 165 mg and comprising 20 wt. % nifedipine, 74.5 wt. % poly(ethylene oxide) of 300,000 molecular weight, 5 wt. % hydroxypropylmethylcellulose of 9,200 molecular weight, and 0.50 wt. % magnesium stearate; a push layer weighing 82.5 mg and comprising 65.3 wt. % poly(ethylene oxide) of 5,000,000 molecular weight, 29.2 wt. % sodium chloride, 5 wt. % hydroxypropylmethylcellulose of 11,200 molecular weight, and 0.5 wt. % magnesium stearate; a semipermeable wall weighing 84.7 mg comprising 40 wt. % cellulose acetate consisting of 39.8% acetyl, 49 wt. % triacetin, 6 wt. % Tween 65, and 5 wt. % poly(ethylene glycol) 400; and an overcoat weighing 6.9 mg consisting of 90 wt. % hydroxypropylmethylcellulose of 12,000 molecular weight, and 10 wt. % poly(ethylene glycol) 8000. The dosage form comprised a pair of elongated slits in spaced apart relation on distant sides of the dosage form. The dosage form had a mean release rate of 2.0 mg/hr for the drug formulation over a 17 hr period. The push layer remained substantially in the dosage form during the drug dispensing period.

EXAMPLE 3

The procedures of the above examples are followed to provide a bilayer layer, drug layer, push layer cores coated by a composition formed from 2594 g of fluid consisting of 88% water, 4.8% cellulose triacetate milled to a fine powder, 5.9% triacetin, 0.7% polysorbate 65, and 0.6% poly (ethylene glycol) 400 applied as an atomized spray at a rate of 8.8 mL/min. The semipermeable wall is immediately coated by applying 400 mL of a second fluid consisting of 93% water, 4.9% hydroxypropylmethylcellulose of 9,200 molecular weight and 2.1% poly(ethylene glycol) applied as an atomized spray at a rate of 4.7 mL/min., to a continuously cascading column held at a temperature of 36° C. by 56° C. heated air directed through the bilayer cores at a rate of 33CFM. The coated tablets are loaded onto stainless steel trays and placed in a forced air oven at 50° C. for 3 days. The dosage forms were removed from the oven and equilibrated to room temperature. Next, a mechanical cutter equipped with a steel cutting blade cut approximately 10 mil deep (0.25 mm), 10 mil wide (0.25 mm) through both coated layers, across both core layers spanning a distance of approximately 130 mils (3.3 mm) on one surface of the dosage from to provide the bilayer exit port, that release drug formulation from the drug layer through the drug dispensing period. The side slit exit dosage forms were tested in distilled water heated to 37° C. The dosage form released at an average delivery rate of 1.5 mg of nifedipine per hour over an extended time of 24 hrs as a ribbon of gelled drug through the slit exit port. The exit port can be manufactured with various shapes to produce a ribbon of corresponding shape, for example a flat ribbon of gelled drug, a tubular ribbon of gelled drug, a curved ribbon of gelled drug, a continuous undulating ribbon of gelled drug, a longer than wide ribbon of gelled drug, and a longer than wide wedged-shaped ribbon of gelled drug.

EXAMPLE 4

1.4 kilograms of cores equivalent to those in Example 1 were charged into pan coater. A coating solution was prepared by dissolving 237.5 grams of cellulose acetate and 12.5 grams of polyethylene in 5,700 grams of acetone and 300 grams of water. The acetyl content of the cellulose acetate was 39.8 weight percent. The molecular weight of the polyethylene glycol was 3,350 grams per mole. The coating solution was sprayed onto the bed of bilayer cores in a current of warm air until 30 mg of membrane coating was applied to each bilayer core of the bed. The resulting bed of cores were removed and dried in a forced air oven to remove the residual coating solvents.

After the coating and drying operation, two samples of these coated and dried systems were removed. In one system, the wall was slit with a razor blade. The single slit was positioned such that it traversed the bilayer core from core land to core land, a span of approximately 3.18 millimeters. The width of the slit was approximately 300 microns. The depth of the slit was sufficient to pierce the wall. A second and separate sample of these coated and dried dosage forms were drilled with a mechanical drill bit. This produced a round orifice having a diameter of 0.51 millimeter positioned in the center of the tablet face on the drug layer side. The depth of the port was sufficient to pierce the wall.

Then, all of the resulting dosage forms were placed in water thermostated to 37 degrees centigrade. The dosage forms with the round ports did not start pumping drug until after 1 hour. By contrast, the side-slit dosage forms started pumping within 0.5 hour. After 24 hours, both systems had released the dosage amount of drug, 30 mg nifedipine.

This experiment demonstrated that side slit dosage forms can produce a faster initial rate of drug release. Dosage forms with small round ports initially release at a slower rate, particularly when the drug is insoluble and is delivered from the dosage form by being extruded as a suspension in an osmogel.

In summary, it will be appreciated the present invention contributes to the dispensing art an unobvious dosage form that possesses practical utility, can administer a drug at a dose metered release rate per unit time. While the invention has been described and pointed out in detail, with reference to operation embodiments thereof, it will be understood by those skilled in the art, that various changes, modifications, substitutions and omissions can be made without departing from the spirit of the invention. It is intended, therefore, that the invention embraces these equivalents within the scope of the claims which follows.

We claim:

1. A dosage form for the delivery of a drug to an animal, wherein the dosage form comprises:
   (a) a wall comprising a semipermeable composition permeable to the passage of fluid and impermeable to the passage of drug, which wall comprises a side that surrounds:
   (b) an interior compartment;
   (c) a drug layer in the compartment comprising a drug and a pharmaceutically acceptable polymer carrier for delivering the drug from the dosage form;
   (d) a push layer in the compartment comprising an osmopolymer that imbibes fluid, expands and pushes the drug layer from the dosage form, the push layer comprising an osmopolymer possessing a higher molecular weight than the polymer in the drug layer; and wherein the dosage form is characterized by:
   (e) exit means in the side of the wall that connects with both the drug layer and the push layer with the exterior of the dosage form.

2. The dosage form for delivering the drug according to claim 1, wherein the drug layer is delivered through the exit means and the push layer remains in the compartment during the drug delivery period.

3. The dosage form for delivering the drug according to claim 1, wherein the exit means is a slit.

4. The dosage form for delivering the drug according to claim 1, wherein the exit means is an elongated aperture.

5. The dosage form for delivering the drug according to claim 1, wherein the exit means is a hole long in proportion to its width.

6. The dosage form for delivering the drug according to claim 1, wherein the exit means is a long narrow cut.

7. The dosage form for delivering the drug according to claim 1, wherein the exit means communicates with the drug layer and the push layer and is formed by laser cutting the semipermeable wall.

8. A dosage form for delivering a drug to an animal, wherein the dosage form comprises:
   (a) a wall comprising a semipermeable composition permeable to the passage of fluid and impermeable to the passage of drug, which wall comprises a side that surrounds:
   (b) an interior compartment;
   (c) a drug layer in the compartment comprising a drug and a pharmaceutically acceptable hydrogel for delivering the drug from the dosage form;
   (d) a push layer in the compartment comprising an osmopolymer, which in operation, imbibes fluid, expands and pushes the drug layer from the dosage form; and wherein the dosage form is characterized by:
   (e) exit means in the side of the wall that communicates with the drug layer and the push layer and delivers a ribbon of gelled drug through the exit means from the dosage form over time, with the push layer remaining in the dosage form.

9. An improvement in a dosage form for delivering a drug to a human, wherein the dosage form comprises:
   (a) a wall comprising a semipermeable composition permeable to the passage of fluid and impermeable to the passage of drug, which wall comprises a side that surrounds:
   (b) a drug layer comprising a drug and a pharmaceutically acceptable carrier;
   (c) a push layer that imbibes fluid comprising an osmopolymer, expands and pushes the drug layer from the dosage form; and wherein the improvement comprises:
   (d) means in the side of the wall that communicates with the drug layer and the push layer for lessening the drug-free time before the dosage form delivers the drug, which means release the drug layer while concomitantly maintaining the push layer in the dosage form, when in operation in the human.

* * * * *